United States Patent
Woods

(10) Patent No.: US 9,522,130 B2
(45) Date of Patent: Dec. 20, 2016

(54) USE OF MIR-221 AND 222 LOWERING AGENTS TO PREVENT CARDIOVASCULAR DISEASE IN DIABETIC SUBJECTS

(71) Applicant: Thomas Cooper Woods, New Orleans, LA (US)

(72) Inventor: Thomas Cooper Woods, New Orleans, LA (US)

(*) Notice: Subject to any disclaimer, the term of this patent is extended or adjusted under 35 U.S.C. 154(b) by 0 days.

(21) Appl. No.: 14/209,586

(22) Filed: Mar. 13, 2014

(65) Prior Publication Data
US 2015/0258056 A1 Sep. 17, 2015

Related U.S. Application Data

(60) Provisional application No. 61/784,422, filed on Mar. 14, 2013.

(51) Int. Cl.
| | |
|---|---|
| *A61K 48/00* | (2006.01) |
| *A61K 31/277* | (2006.01) |
| *A61K 31/00* | (2006.01) |
| *C12N 15/113* | (2010.01) |
| *A61K 45/06* | (2006.01) |
| *A61K 31/436* | (2006.01) |
| *C12N 15/11* | (2006.01) |
| *A61K 31/275* | (2006.01) |

(52) U.S. Cl.
CPC ............ *A61K 31/277* (2013.01); *A61K 31/00* (2013.01); *A61K 31/275* (2013.01); *A61K 31/436* (2013.01); *A61K 45/06* (2013.01); *C12N 15/111* (2013.01); *C12N 15/113* (2013.01); *C12N 15/1135* (2013.01); *C12N 2310/113* (2013.01); *C12N 2320/30* (2013.01)

(58) Field of Classification Search
None
See application file for complete search history.

(56) References Cited

U.S. PATENT DOCUMENTS

| | | | |
|---|---|---|---|
| 2005/0261218 A1* | 11/2005 | Esau et al. | 514/44 |
| 2009/0043379 A1 | 2/2009 | Prescott | |
| 2011/0105521 A1 | 5/2011 | Garcia-Echeverria et al. | |
| 2012/0121530 A1 | 5/2012 | Klein et al. | |
| 2012/0157514 A1 | 6/2012 | Esau et al. | |

OTHER PUBLICATIONS

Diabetes Control and Complications Trial, and Epidemiology of Diabetes Interventions and Complications Research Group. "Intensive diabetes therapy and carotid intima-media thickness in type 1 diabetes mellitus." The New England journal of medicine 348.23 (2003): 2294.*
Liu et al. (Circulation Research Feb. 27, 20098 476-487).*
Wang et al. (J. Cellular Biochemistry 2012, 113:2040-2046).*
Luo et al. (Mol and Cell. Bio Dec. 1996, 6. 6774-6751).*
Li et al., MicroRNA-221 regulates high glucose-enduced endothelial dysfunction. Biochem Biophys Res Common. Mar. 27, 2009, vol. 381, No. 1, pp. 81-83. (author manuscript) p. 3, para 4.
Stinson et al. TRPS1 targeting by miR-221/222 promotes the epithelial-to-mesenchymal transition in breast cancer. Science Signaling. Jun. 14, 2011, vol. 4, No. 177, p. ra41, p. 5, para 2.

* cited by examiner

*Primary Examiner* — Kimberly Chong
(74) *Attorney, Agent, or Firm* — Juan J. Lizarraga

(57) ABSTRACT

The present invention relates to methodology for preventing increased cardiovascular disease in subjects with diabetes mellitus. The methods include the use of compounds to inhibit activation of the extracellular response kinase pathway, activate 5' adenosine monophosphate protein kinase, and inhibit microRNA-221 and microRNA-222 for the purpose of reducing microRNA-221 and -222 levels in the vasculature. Reduction of microRNA-221 and -222 in the vasculature of diabetic patients restores normal levels of intimal thickening and enhances the effectiveness of the standard of care in diabetic subjects.

6 Claims, 14 Drawing Sheets

SEQUENCE LISTING

<160> NUMBER OF SEQ ID NOS: 4

<210> SEQ ID NO 1
<211> LENGTH: 21
<212> TYPE: RNA
<213> ORGANISM: Artificial Sequence
<220> FEATURE:
<223> OTHER INFORMATION: Sequence is a synthetic oligonucleotide
<220> FEATURE:
<221> NAME/KEY: misc_RNA
<222> LOCATION: (1)..(21)
<223> OTHER INFORMATION: Sequence is a synthetic oligonucleotide
<300> PUBLICATION INFORMATION:
<301> AUTHORS: Ji R, Cheng Y, Yue J, Yang J, Liu X, Chen H, Dean DB,
       Zhang C.
<302> TITLE: MicroRNA expression signature and antisense-mediated
       depletion reveal an essential role of microRNA in vascular
       neointimal lesion formation.
<303> JOURNAL: Circulation Research
<304> VOLUME: 100
<305> ISSUE: 11
<306> PAGES: 1579-1588
<307> DATE: 2007-06-08

<400> SEQUENCE: 1
acccaguagc cagauguagc u                                          21

<210> SEQ ID NO 2
<211> LENGTH: 21
<212> TYPE: RNA
<213> ORGANISM: Artificial Sequence
<220> FEATURE:
<223> OTHER INFORMATION: Sequence is a synthetic oligonucleotide with a
       locked nucleic acid backbone
<220> FEATURE:
<221> NAME/KEY: modified_base
<222> LOCATION: (1)..(21)
<223> OTHER INFORMATION: Sequence is a synthetic oligonucleotide with a
       locked nucleic acid backbone
<300> PUBLICATION INFORMATION:
<301> AUTHORS: Ji R, Cheng Y, Yue J, Yang J, Liu X, Chen H, Dean DB,
       Zhang C.
<302> TITLE: MicroRNA expression signature and antisense-mediated
       depletion reveal an essential role of microRNA in vascular
       neointimal lesion formation.
<303> JOURNAL: Circulation Research
<304> VOLUME: 100
<305> ISSUE: 11
<306> PAGES: 1579-1588
<307> DATE: 2007-06-08

<400> SEQUENCE: 2
acccaguagc cagauguagc u                                          21

<210> SEQ ID NO 3
<211> LENGTH: 21
<212> TYPE: RNA
<213> ORGANISM: Artificial Sequence
<220> FEATURE:
<223> OTHER INFORMATION: Sequence is a synthetic oligonucleotide with a
       locked nucleic acid backbone
<220> FEATURE:
<221> NAME/KEY: modified_base
<222> LOCATION: (1)..(21)
<223> OTHER INFORMATION: Sequence is a synthetic oligonucleotide with a
       locked nucleic acid backbone
<300> PUBLICATION INFORMATION:
<301> AUTHORS: Ji R, Cheng Y, Yue J, Yang J, Liu X, Chen H, Dean DB,
       Zhang C.
<302> TITLE: MicroRNA expression signature and antisense-mediated
       depletion reveal an essential role of microRNA in vascular
       neointimal lesion formation.
<303> JOURNAL: Circulation Research
<304> VOLUME: 100

```
<305> ISSUE: 11
<306> PAGES: 1579-1588
<307> DATE: 2007-06-08

<400> SEQUENCE: 3
acccaguagc cagauguagc u                                              21

<210> SEQ ID NO 4
<211> LENGTH: 21
<212> TYPE: RNA
<213> ORGANISM: Artificial Sequence
<220> FEATURE:
<223> OTHER INFORMATION: Modified backbone with 2'-O-methyladenosine for
      a, 2'-O-methylguanosine for g, 2'-O-methylcytodine for c, and
      2'-O-methyluridine for u
<220> FEATURE:
<221> NAME/KEY: modified_base
<222> LOCATION: (1)..(21)
<223> OTHER INFORMATION: Modified backbone with 2'-O-methyladenosine for
      a, 2'-O-methylguanosine for g, 2'-O-methylcytodine for c, and
      2'-O-methyluridine for u
<300> PUBLICATION INFORMATION:
<301> AUTHORS: Ji R, Cheng Y, Yue J, Yang J, Liu X, Chen H, Dean DB,
      Zhang C.
<302> TITLE: MicroRNA expression signature and antisense-mediated
      depletion reveal an essential role of microRNA in vascular
      neointimal lesion formation.
<303> JOURNAL: Circulation Research
<304> VOLUME: 100
<305> ISSUE: 11
<306> PAGES: 1579-1588
<307> DATE: 2007-06-08

<400> SEQUENCE: 4
acccaguagc cagauguagc u                                              21
```

USE OF MIR-221 AND 222 LOWERING AGENTS TO PREVENT CARDIOVASCULAR DISEASE IN DIABETIC SUBJECTS

This application claims priority from U.S. Provisional Application No. 61/784,422 (the '422 application), filed Mar. 14, 2013. The '442 application is incorporated herein by reference.

BACKGROUND OF THE INVENTION

The numbers in parenthesis refer to the numbered references listed at the end of the specification.

Mortality from cardiovascular diseases (CVD) is two to four times higher in patients with diabetes mellitus (1). One component of the cardiovascular disease, intimal thickening (also known as intimal hyperplasia and neointimal formation), is increased in diabetics. Diffuse intimal thickening creates a fertile environment for the initial lipid deposition that occurs early in cardiovascular disease ((2-4) and pathological intimal thickening enhances plaque stability while also increasing plaque burden as cardiovascular disease progresses (5, 6). Additionally, increased intimal thickening is also a major limiting factor to the efficacy of percutaneous coronary interventions (PCI) as it leads to restenosis, the re-sealing of an artery after PCI (7, 8). Thus, there is a need for methods that prevent the increased intimal thickening in diabetic patients.

SUMMARY OF THE INVENTION

This invention is based, in part, on the discovery that one aspect of diabetes mellitus is an increase in microRNA-221 and microRNA-222 (together referred to as miR-221/222) in the arteries. Increases in miR-221/222 lead to accelerated intimal thickening and reduce the effectiveness of the standard of care for prevention of cardiovascular disease. Furthermore this invention is based, in part, on the discovery that a) this increase in miR-221/222 occurs due to an increase in the activity of the protein kinase pathway consisting of Ras, raf-1, Mitogen Activated Kinase Kinase (MEK)-1 and MEK-2, Extracellular signal Response Kinase (ERK)-1 and ERK-2 (collectively referred to as the ERK pathway); and b) that the increase in miR-221/222 in the vasculature can be inhibited by activation of 5' adenosine monophosphate-activated protein kinase (AMPK). Inhibition of the ERK pathway, activation of AMPK, or direct inhibition of miR-221/222 reduces intimal thickening to levels similar to that seen in non-diabetics.

The present invention is a method of inhibiting the increase in miR-221/222 in the vasculature of diabetic patients for the purpose of preventing accelerated cardiovascular disease through inhibition of ERK pathway, direct inhibition of miR-221/222, or activation of AMPK.

The ERK pathway consists of a series of proteins that are activated in response to a stimulus. The ERK pathway has multiple stimuli that promote the activation of the small GTPase, ras, which in turn activates Raf. Raf then activates MEK 1 and 2, which in turn activates ERK 1 and 2 (also known as mitogen activated protein kinase p42/44). A novelty of this invention is that while previous reports suggest that inhibition of the ERK pathway with the MEK1/2 inhibitor, PD98059, is not effective in reducing the cell proliferative aspect of intimal thickening following arterial injury in non-diabetic animals (9), under diabetic conditions the ERK pathway becomes dominant in regulating intimal thickening. The present invention is derived from the finding and includes a method using inhibition of activation of any member of the ERK pathway to lower miR-221/222 levels in the vasculature and in turn reduce the increased intimal thickening that occurs in response to diabetes.

As such, one embodiment of the invention comprises a method using a composition selected from the group of raf inhibitors that include Sorafenib Tosylate (Bay 43-9006, Nexavar), PLX4032 (Vemurafenib, RG7204, Zelboraf, RO5185426), SB 590885 (5-[2-[4-[2-(Dimethylamino) ethoxy]ph-enyl]-5-(4-pyridinyl)-1H-imidazol-4-yl]-2,3-dihydr-o-1H-inden-1-one oxime), GDC 0879 ((E)-2,3-Dihydro-5-[1-(2-hydroxyethy-1)-3-(4-pyridinyl)-1H-pyrazol-4-yl]-1H-inden-1-one-oxime), GW 5074 (3-(3,5-Dibromo-4-hydroxy-benzyliden-e)-5-iodo-1,3-dihydro-indol-2-one), L-779,450 (2-Chloro-5-[2-Phenyl-5-(4-pyridinyl-)-1H-imidazol-4-yl]phenol), ZM 336372 (3-(Dimethylamino)-N-[3-[(4-hydroxyb-enzoyl)-amino]-4-methylphenyl]benzamide), PLX-4720, RAF265 (CHIR-265), NVP-BHG712, and AZ628.

Another embodiment of the invention comprises a method using a composition selected from the group of MEK inhibitors that include AZD6244 (Selumetinib, ARRY-142886), PD0325901 (PD325901), CI-1040 (PD 184352), U0126, PD98059, GSK1120212 (JTP-74057, trametinib), BIX02188, BIX02189, AS703026, and AZD8330 (ARRY-424704). Additionally, one embodiment of the invention comprises a method using a composition that inhibits ERK.

Another embodiment of the invention is a method using a composition that activates AMPK. This composition can be selected from the group of AMPK agonists: metformin, AICAR, and or A-769662.

Another embodiment of the invention includes methods that directly inhibit miR-221/222 through silencing RNA (siRNA) methods. Silencing RNA are small ribonucleic acids that are designed to bind to other nucleic acids and either inhibit their function or promote their degradation. In order to promote stability and efficacy of these silencing RNAs, their structure is often modified. These modifications include changes to the nucleic acid backbone to a phosphorothioate, 2'-O methylation (2'OMe) or locked nucleic acids.

Intimal thickening is the major cause for failure of PCI and this is exaggerated in diabetic patients. Thus, another embodiment of the invention is a method for treating or preventing restenosis and vascular stenosis in subjects with diabetes mellitus comprising administering a therapeutically effective amount of a compound that reduces miR-221 and/or miR-222 levels in the vasculature combined with an inhibitor of mTOR. This mTOR inhibitor may be selected from a group consisting of BEZ235 (NVP-BEZ235), Everolimus (RAD001), Rapamycin (Sirolimus, AY-22989, WY-090217), AZD8055, Temsirolimus (CCI-779, Torisel), PI-103, KU-0063794, Deforolimus (Ridaforolimus, AP23573, MK-8669), PP242, XL765, GSK1059615, WYE-354, OSI-027, GDC-0980 (RG7422), GSK2126458, PKI-587, PF-04691502, WYE-125132, WYE-687, NVP-BGT226, WAY-600, AZD2014, INK 128, Torin1.

The standard of care for preventing restenosis is the use of drug eluting stents that release an anti-restenotic agent over a prolonged period. Thus another embodiment of the invention is a method for treating or preventing restenosis and vascular stenosis in subjects with diabetes mellitus comprising insertion of an intraluminal device impregnated with and configured to release a compound that inhibits increases in miR-221 and/or miR-222 in the vasculature and an mTOR inhibitor.

DETAILED DESCRIPTION OF THE INVENTION

The present invention provides methods for the prevention and treatment of cardiovascular disease in patients with diabetes mellitus. As used herein, the term "cardiovascular disease" refers to pathological processes that lead to a restriction of blood flow through the blood vessel. This restriction may result from the development of an atherosclerotic plaque or through restenosis. In both cases intimal thickening plays an important role in the development and progress of the cardiovascular disease and the restriction of blood flow.

Intimal thickening is the growth of the innermost layer of the artery wall. The artery wall consists of three layers. The outer most is the adventia, which holds the artery in place. The middle layer is the media. This layer consists largely of vascular smooth muscle cells (VSMCs) that function to dilate and constrict the artery as needed. The innermost layer is the intima and includes the endothelium that forms a barrier between the blood and the artery. Intimal thickening consists of VSMC migrating from the media to the intima and proliferating. As the cells proliferate, the intima becomes thicker and lumen of artery narrows restricting blood flow.

Atherosclerotic plaque development occurs when lipids (e.g. cholesterol) are deposited in the artery wall and elicit an inflammatory response in the cells that comprise the artery wall. This inflammatory response leads to the recruitment of circulating inflammatory cells and increased intimal thickening. Together these processes lead to the development of lesion within the artery wall that contains a necrotic core that develops from the processing of the lipids by the inflammatory cells that is surrounded by vascular smooth muscle cells that form a "fibrous cap" that stabilizes the plaque. Continued growth of this lesion leads to a narrowing of the arterial lumen and a restriction of blood flow. At this point, the restriction of blood flow can lead to ischemia in the organs supplied by the blood vessel resulting in angina or claudication. Ultimately, the fibrous cap erodes away and a rupture occurs which leads to myocardial infarction (heart attack) and stroke.

Figure 1:
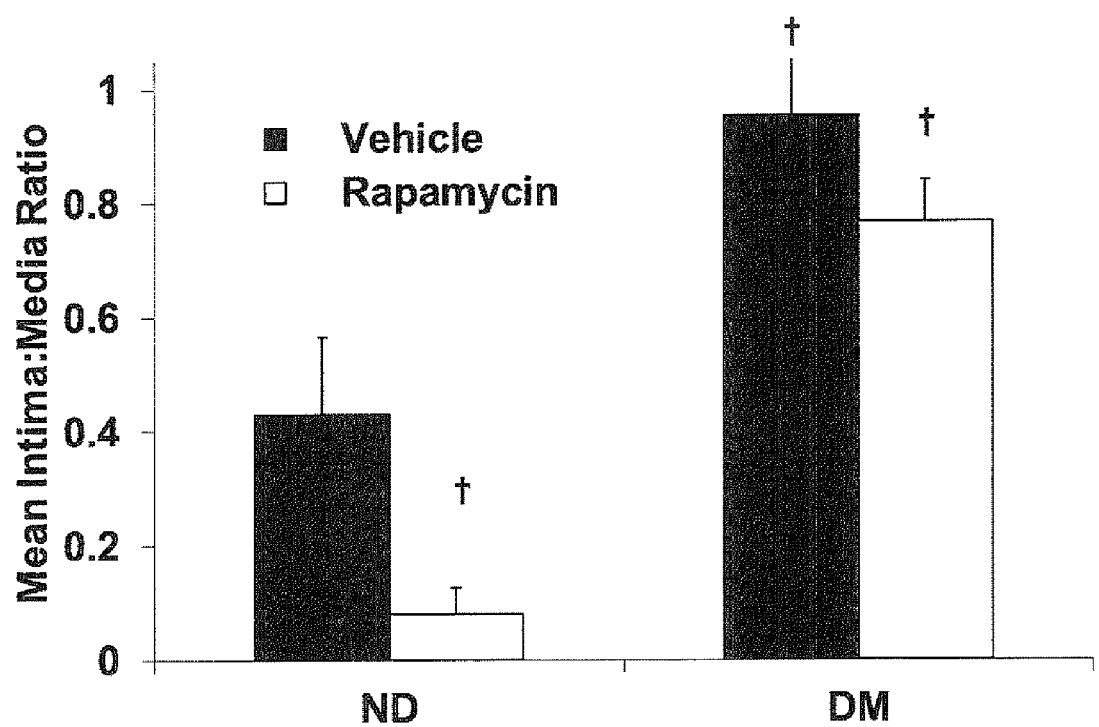
FIG. 1. Neointimal hyperplasia is increased in an mTOR-independent manner in diabetic mice. Femoral artery wire injury was performed in the mice in diabetic mice (DM) and non-diabetic mice (DM) and neointima formation was assessed at 14 days post-injury. Injury resulted in a significant increase in neointima formation in the DM compared to ND mice. Intraperitoneal (IP) injection of rapamycin (4 mg/kg/d) was effective in significantly reducing intimal hyperplasia in controls but not the diabetic mice. Data represent the mean±SEM. † indicates p<0.05 by ANOVA with Tukey's HSD.
Figure 2:
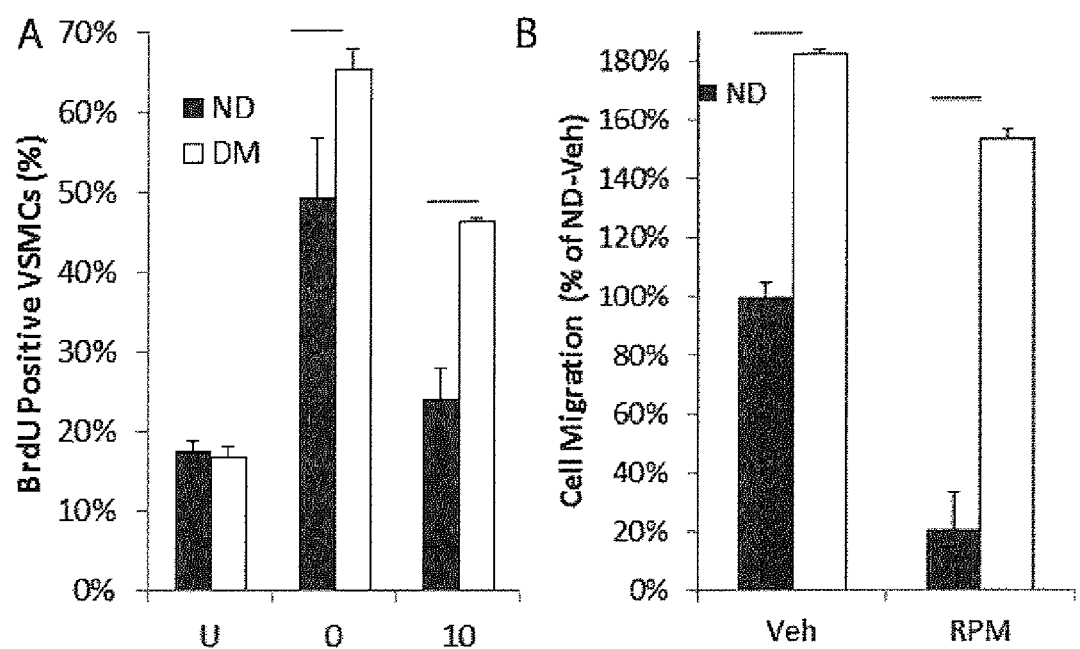
FIG. 2. VSMCs from diabetic mice exhibit a diabetic phenotype. A) Proliferation of the same VSMCs stimulated with DMEM supplemented with 20% fetal bovine serum with and without rapamycin (0 and 10 nM) for 7 d compared to unstimulated VSMCs (U). B) Chemotaxis toward PDGF (10 ng/mL) of the above VSMCs after pretreatment with vehicle or rapamycin for 24 h.

Restenosis refers to the re-narrowing of a blood vessel following treatment of a narrowing (stenosis) with percutaneous intervention (e.g. balloon angioplasty). In this case, intimal thickening is the major factor driving blood vessel narrowing. The inflation of a balloon at the site of a vascular stenosis leads to an inflammatory response that drives increased intimal thickening. This form of intimal thickening is often referred to as neointimal hyperplasia, as it represents the accelerated proliferation (hyperplasia) of VSMCs to form a new intima. FIG. 1 illustrates that intimal thickening in response to injury to the artery is increased in a mouse model of diabetes. It further shows that inhibition of the mammalian target of rapamycin (mTOR) which is highly effective at blocking intimal thickening in non-diabetics is no longer effective in the diabetic mouse model. FIG. 2 shows that VSMCs isolated from the mouse model of diabetes exhibit increased proliferation and migration compared to VSMCs isolated from non-diabetic mice and a resistance to the effects of the mTOR inhibitor, rapamycin. These results mimic clinical findings with mTOR inhibitor eluting stents that show an increase in restenosis in the diabetic population (10-13).

Figure 3:
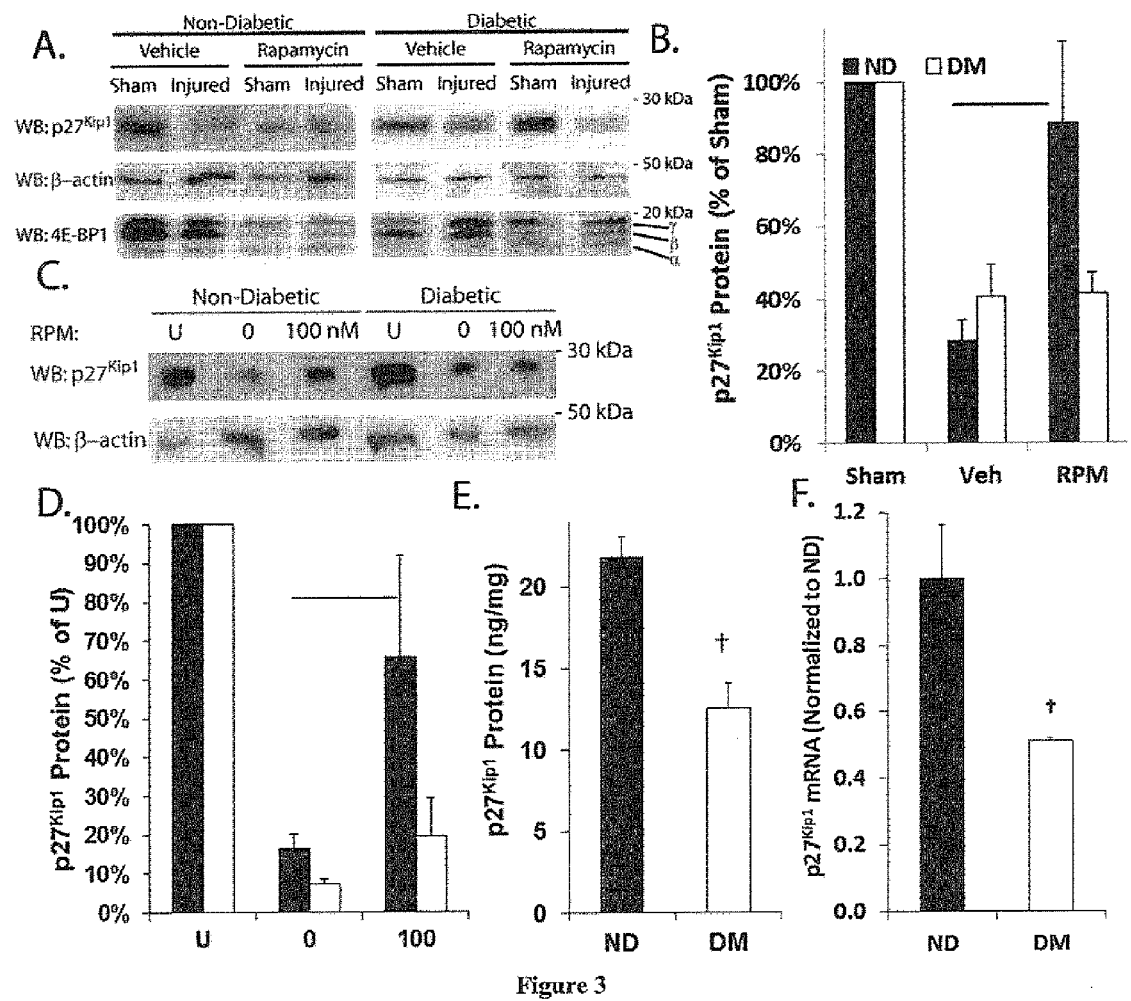
FIG. 3. Regulation of $p27^{Kip1}$ by mTOR is lost in diabetic mice. Representative western blots (A) and densitometric measurement (B) of $p27^{Kip1}$, 4E-BP1, and β-actin in the femoral arteries of diabetic (DM) and non-diabetic (ND) mice following femoral artery wire injury or a sham procedure with and without daily injections of rapamycin (4 mg/kg/d). C and D) Representative western blots (C) and densitometric measurement (D) of $p27^{Kip1}$ and β-actin in VSMCs isolated from diabetic (DM) and non-diabetic (ND) mice following stimulation with DMEM supplemented with 20% FBS with and without 100 nM rapamycin compared to unstimulated controls. E and F) $p27^{Kip1}$ protein (E) and mRNA (F) in the aortae of diabetic and nondiabetic mice. Bars and † indicate p<0.05 by ANOVA (B and D) or Student's t-test (E and F).

Multiple aspects of diabetes result in an inflammatory insult to the vasculature, including hyperglycemia (14), hypoglycemia (15-17), inflammation (15, 18), and reactive oxygen species (19-21). While it is clear that this increased injury to the vasculature promotes increased cardiovascular disease in diabetic patients, changes in the cellular and molecular responses to these insults may also play an important role in the increased cardiovascular disease in the diabetic population (20, 22, 23). The present invention is a method for preventing the increased intimal thickening that occurs in diabetic patients. VSMC proliferation and migration are regulated by the cyclin dependent kinase inhibitor, $p27^{Kip1}$. Quiescent VSMCs maintain an elevated level of $p27^{Kip1}$ that blocks VSMC proliferation and migration and inhibits neointimal hyperplasia (24-29). Upon injury, $p27^{Kip1}$ protein is down regulated through the activation of the mammalian Target of Rapamycin (mTOR) as neointimal hyperplasia progresses (24-27). Inhibition of mTOR restores normal $p27^{Kip1}$ levels, blocks VSMC proliferation and migration and is effective in the prevention of in-stent restenosis (27, 30-32). FIGS. 3A and 3B illustrate that the ability of inhibition of mTOR to produce an increase in $p27^{Kip1}$ in injured arteries, as seen in the non-diabetic mice, is lost in diabetic mice. FIGS. 3C and 3D illustrate that the loss of effect of mTOR inhibition on $p27^{Kip1}$ levels is also seen in VSMCs isolated from these mice. FIG. 3E demonstrates that the $p27^{Kip1}$ protein levels are reduced in uninjured arteries of diabetic mice compared to non-diabetic mice. FIG. 3F demonstrates that mRNA encoding $p27^{Kip1}$ is also reduced in the vasculature of diabetic mice, Together these data demonstrate that diabetes promotes a decrease in $p27^{Kip1}$ protein, in the absence of injury to the vasculature, through a loss of $p27^{Kip1}$ mRNA. This explains the resistance to the mTOR inhibitor rapamycin seen in FIG. 1, as mTOR inhibitors increase $p27^{Kip1}$ protein by blocking protein degradation. Inhibition of mTOR will not increase $p27^{Kip1}$ protein levels when $p27^{Kip1}$ mRNA is reduced. The present invention is a method for restoring normal regulation of $p27^{Kip1}$ protein in diabetic patients.

Figure 4:
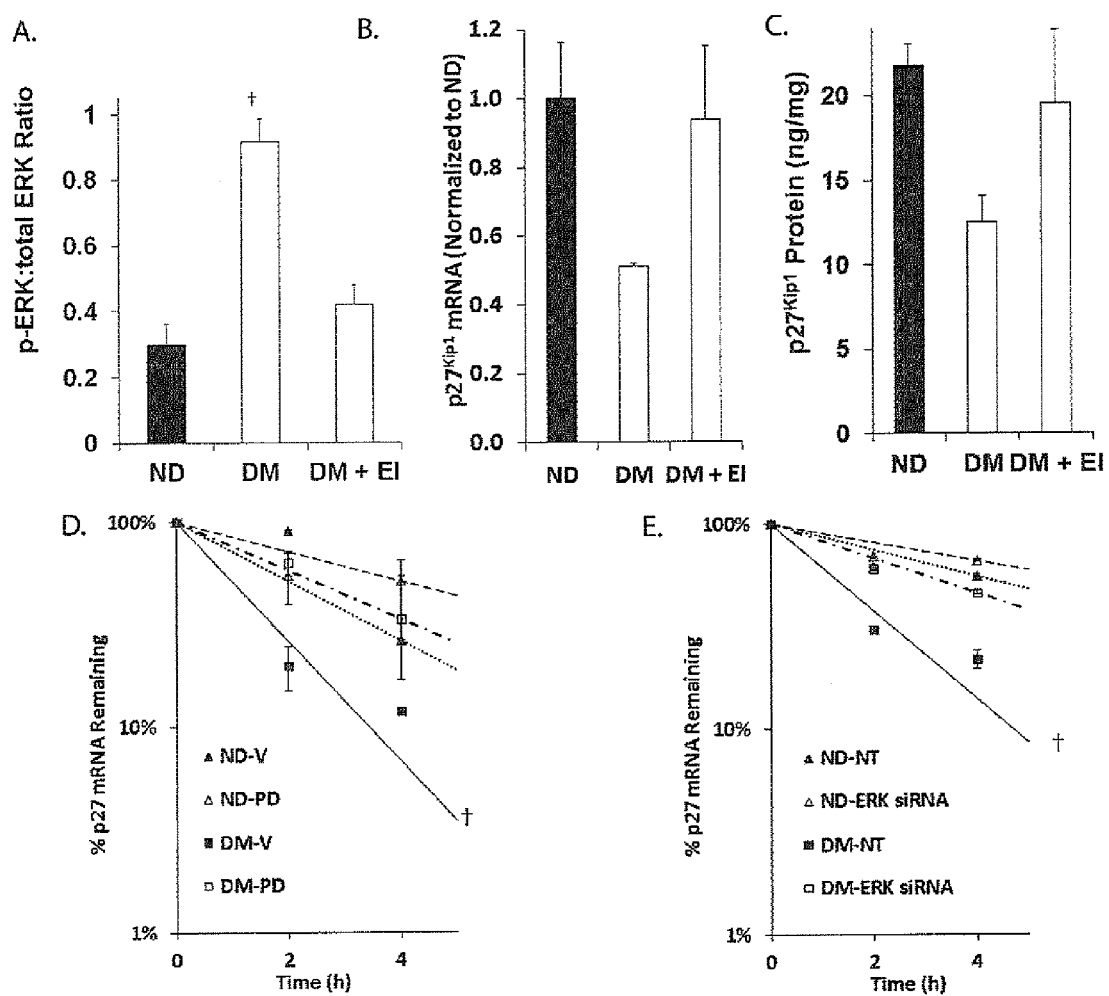
FIG. 4. Increased ERK activation promotes loss of $p27^{Kip1}$ in diabetic mice. A) The ratio of phosphorylated (active) ERK to total ERK in the aortae of non-diabetic (ND) mice and diabetic mice receiving either vehicle (DM) or the ERK pathway inhibitor (DM+EI) U0126, ip, 7.5 mg/kg/d for 3 days). $p27^{Kip1}$ protein (B) and mRNA (C) levels in the same mice as in A. D and E) The half-life of $p27^{Kip1}$ mRNA in VSMCs from DM and ND mice stimulated with serum with and without the ERK pathway inhibitor PD98059 (D,PD) or siRNA targeting ERK (E, ERK siRNA). † indicate p<0.05 by ANOVA (B and D) or Student's t-test (E and F).

FIG. 4A shows that in the diabetic mice there is an increased activation of the extracellular response kinase 1/2 (ERK) pathway, as has been previously reported (11, 12, 33). FIGS. 4B and 4C demonstrate that treatment of diabetic mice with an inhibitor MEK 1/2 which blocks activation of the ERK pathway restores normal levels of $p27^{Kip1}$ mRNA and protein in the diabetic mice. FIG. 4D illustrates that the reduced $p27^{Kip1}$ mRNA seen in VSMCs from the diabetic mice results from accelerated degradation rather than decreased mRNA production. Further FIG. 4D demonstrates that inhibition of the ERK pathway with PD98059, a MEK 1/2 inhibitor, is effective at blocking the accelerated degradation of $p27^{Kip1}$ mRNA. Likewise, FIG. 4E shows that inhibition of ERK 1/2 directly with silencing RNA inhibits the accelerated degradation of $p27^{Kip1}$ mRNA in VSMCs from diabetic mice. Thus, elevated activation of the ERK pathway promotes the loss of $p27^{Kip1}$ that leads to increased intimal thickening in diabetes. This invention provides methodology to prevent the loss of $p27^{Kip1}$ in the vasculature of diabetic patients and the subsequent increased intimal thickening.

The present invention includes the administrator of "therapeutically effective amounts" of compounds in order to inhibition ERK pathway activation, activate AMPK, or directly inhibit miR-221/222. Therapeutically effective amounts are defined as doses that achieve concentrations in the vasculature at or above the half maximal inhibitory concentration (IC50).

Figure 5:
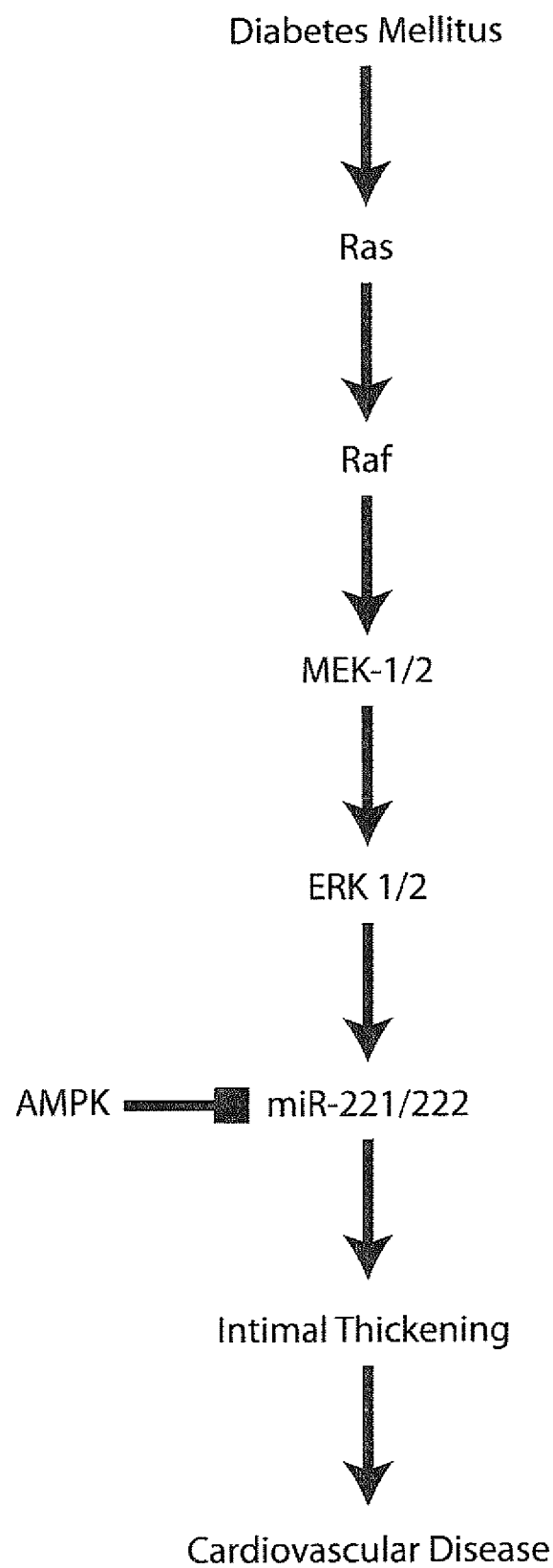
FIG. 5. Molecular mechanism related to the increase in miR-221/222 in the vasculature of subjects with diabetes mellitus. Diabetes mellitus leads to an increase in activation of Ras which then activates Raf. Raf then activates MEK1/2. MEK 1/2 activates ERK 1/2 which in turn leads to an increase in miR-221/222. Inhibition of any of these targets will block the increase in miR-221/222 that occurs in diabetes mellitus. Activation of AMPK by an AMPK agonist will also reduce miR-221/222.

The ERK pathway, illustrated in FIG. 5, has multiple stimuli that promote activate the small GTPase, Ras, which in turn activates Raf. Raf then phosphorylates a mitogen activated protein kinase kinase (MEK 1 and MEK 2), which in turn activates ERK 1/2 (also known as mitogen activated protein kinase). One embodiment of the present invention is a method comprising inhibition of the ERK pathway. This can be achieved through inhibition of activation of any member of the ERK pathway. Thus, one embodiment of this invention is a method using a composition selected from the group of raf inhibitors that include Sorafenib Tosylate (Bay 43-9006, Nexavar), PLX4032 (Vemurafenib, RG7204, Zelboraf, RO5185426), SB 590885 (5-[2-[4-[2-(Dimethylamino)ethoxy]ph-enyl]-5-(4-pyridinyl)-1H-imidazol-4-yl]-2,3-dihydr-o-1H-inden-1-one oxime), GDC 0879 ((E)-2,3-Dihydro-5-[1-(2-hydroxyethy-1)-3-(4-pyridinyl)-1H-pyrazol-4-yl]-1H-inden-1-one-oxime), GW 5074 (3-(3,5-Dibromo-4-hydroxy-benzyliden-e)-5-iodo-1,3-dihydro-indol-2-one), L-779,450 (2-Chloro-5-[2-Phenyl-5-(4-pyridinyl-)-1H-imidazol-4-yl]phenol), ZM 336372 (3-(Dimethylamino)-N-[3-[(4-hydroxyb-enzoyl)-amino]-4-methylphenyl]benzamide), PLX-4720, RAF265 (CHIR-265), NVP-BHG712, and AZ628. Another embodiment of the invention comprises a method using a composition selected from the group of MEK inhibitors that include AZD6244 (Selumetinib, ARRY-142886), PD0325901 (PD325901), CI-1040 (PD 184352), U0126, PD98059, GSK1120212 (JTP-74057, trametinib), BIX02188, BIX02189, AS703026, and AZD8330 (ARRY-424704). Two additional embodiments of the invention comprise methods using a composition that inhibits ERK or Ras.

Figure 6:
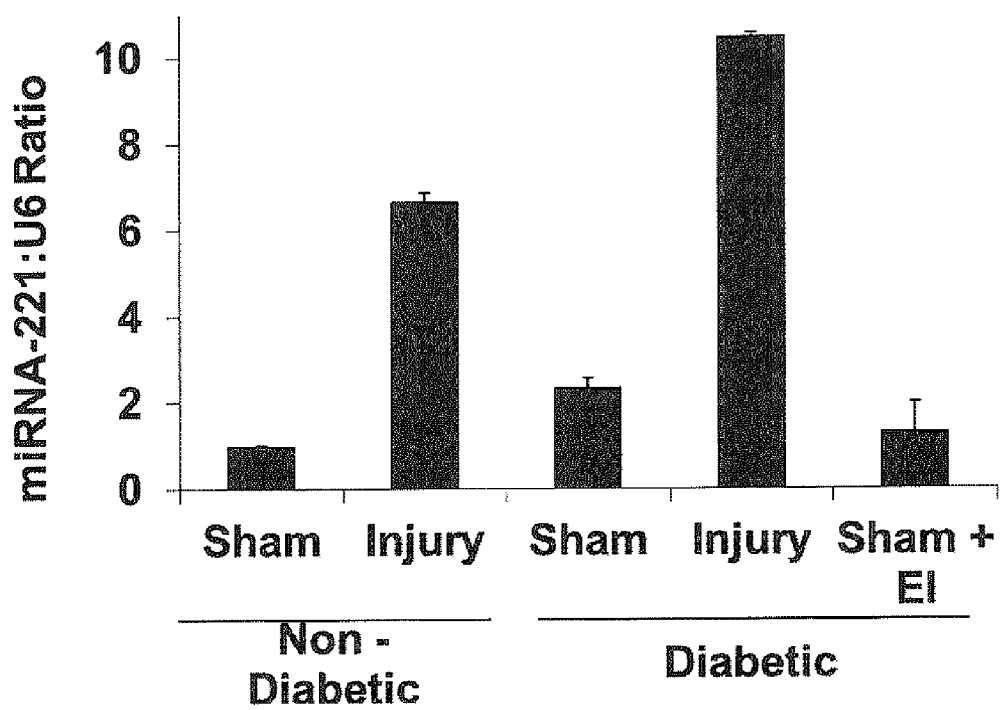
FIG. 6. Arterial miR-221/222 is increased in an ERK-dependent manner in diabetic mice. Femoral artery wire injury or sham procedure was performed in the non-diabetic (ND) and diabetic (DM) mice and miR-221 levels were measured 3d post-injury. A group of MF-12 mice (Sham+EI) received a MEK1 inhibitor (U0126, 7 rag/kg/d). Data represent the mean±SEM.
Figure 7:
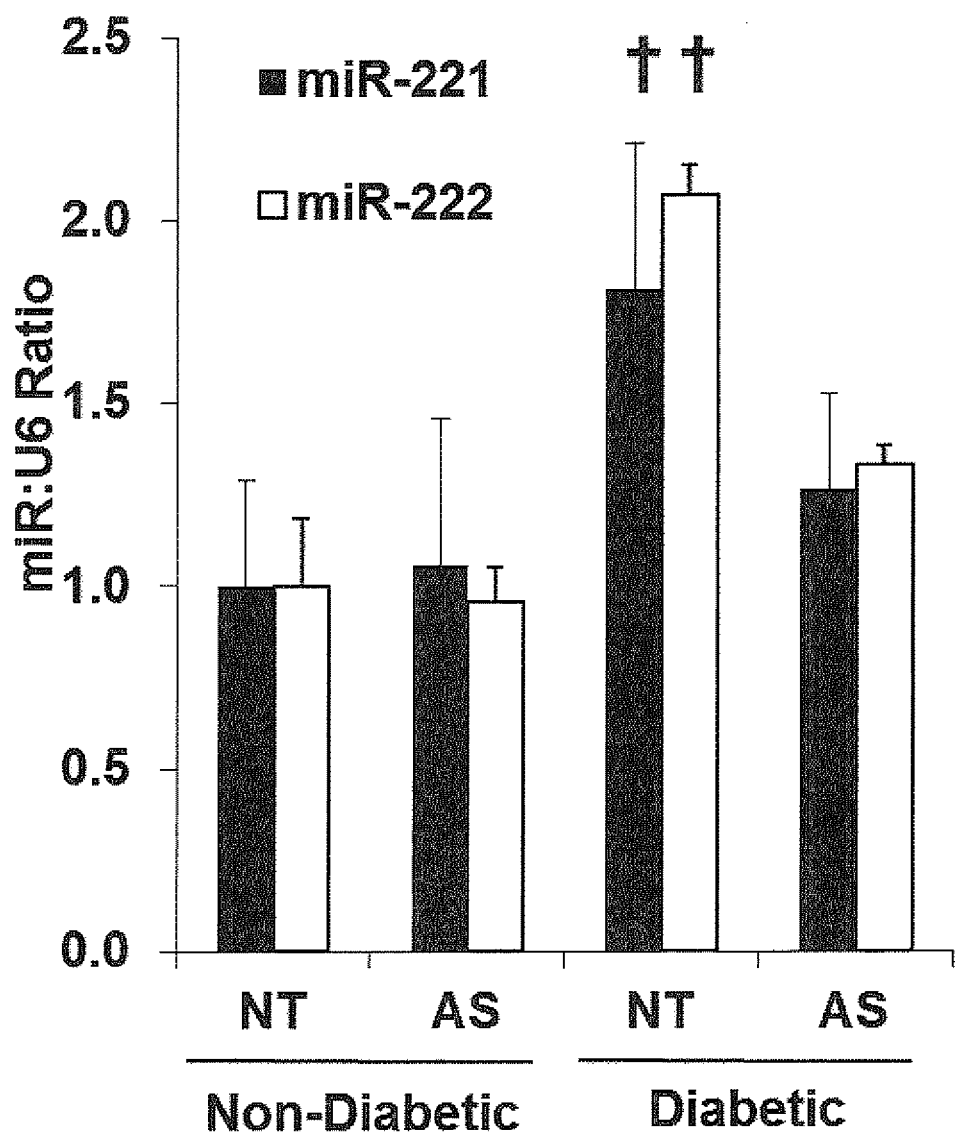
FIG. 7. Diabetes induces an increase in miR-221/222 levels in arteries. Total RNA was prepared from injured femoral arteries of diabetic and non-diabetic mice receiving a Pluronic gel containing either control oligonucleotide (NT) or 2'OMe-miR-222 (AS) for 7 days. Levels of miR-221 and miR-222 were measured using quantitative real-time PCR with U6 as a loading control. Data is normalized to the ND. Data represent the mean±SEM and † indicates p<0.05 by ANOVA using Tukey's HSD.

Increased ERK pathway activity promotes an increase in two microRNAs known to promote intimal thickening, miR-221 and miR-222 (miR-221/222). miR-221/222 accelerate intimal thickening through degradation of $p27^{Kip1}$ mRNA. FIG. 6 demonstrates that diabetic mice exhibit increased levels of miR-221/222 in the vasculature compared to non-diabetic mice both before and after injury and that this increase is blocked by administration of the MEK 1/2 inhibitor, U0126. FIG. 7 demonstrates that both miR-221/222 are elevated in the vasculature of diabetic mice and that treatment with a silencing RNA, 2'-OMe-miR-222, reduces miR-221/222 levels back to normal.

Silencing RNA (siRNA) is an effective method for inhibition of microRNA activity (34). One embodiment of this invention is the use of silencing RNA in this manner to directly inhibit the increase in miR-221/222 in the vasculature of diabetic patients. This silencing RNA will be comprised of the ribonucleic acid sequence: 5'-ACCCA-GUAGCCAGAUGUAGCU-3' as described in SEQ ID NO 1, where A is adenosine, C is cytosine, G is guanine, and U is uridine. The silencing RNA may consist of a ribonucleic acid with a phosphorothioate as described in SEQ ID NO 2, locked nucleic acid as described in SEQ ID NO 3, or 2'-O-methylated backbone as described in SEQ ID NO 4. In the phosphorothioate, a sulfur is substituted for a non-bridging oxygen in the phosphate backbone of an oligonucleotide. A 2'O-methylated RNA is a ribonucleic acid where a methyl group has been added to the 2' hydroxyl group of the ribose unit. A locked nucleic acid is a nucleic acid where the nucleotide is modified with an extra bridge connecting the 2' oxygen and 4' carbon.

Figure 8:
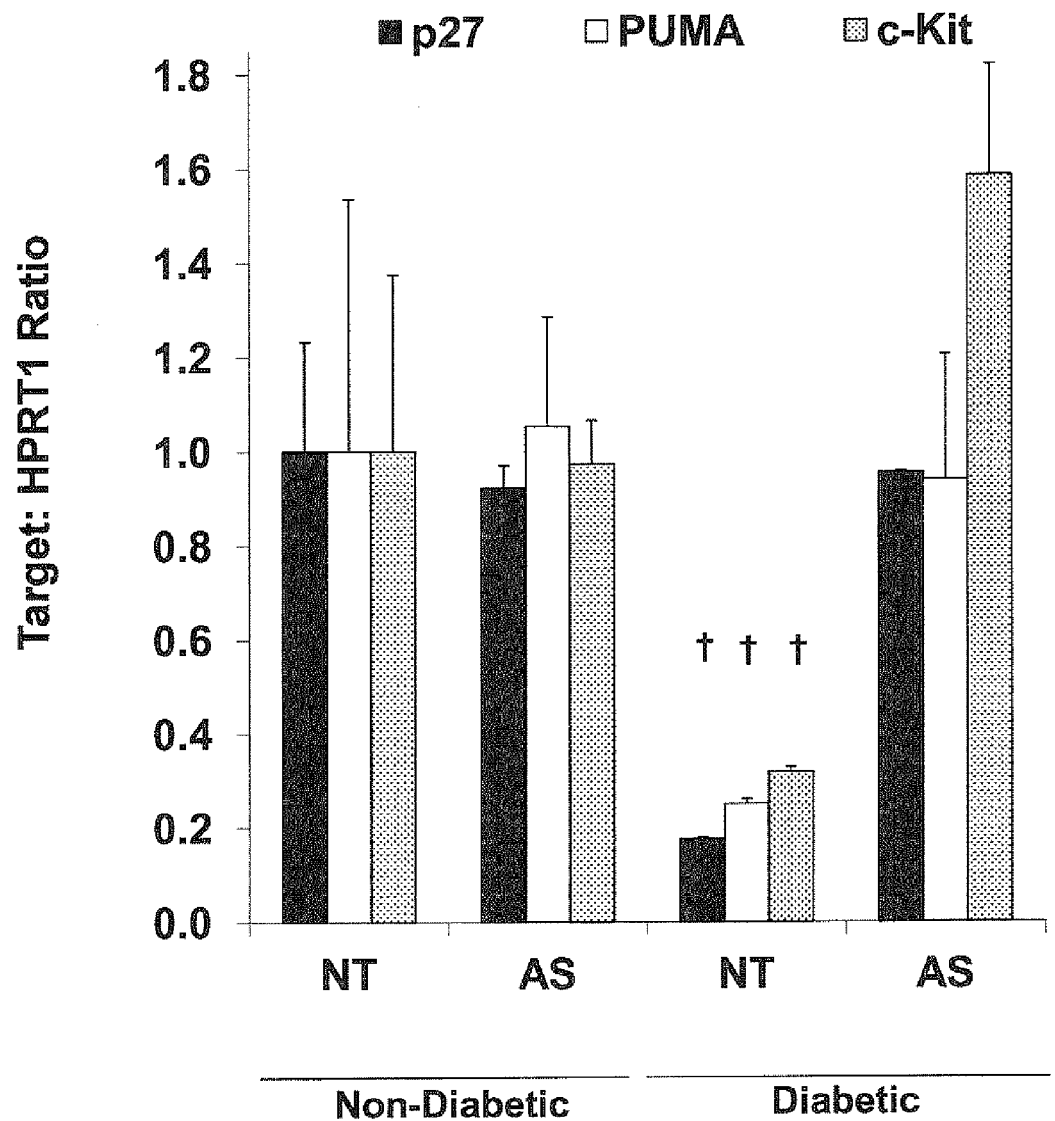
FIG. 8. Diabetes induces an increase in miR-221/222 that reduces $p27^{Kip1}$, c-Kit, and PUMA levels. Total RNA was prepared from injured femoral arteries of diabetic and non-diabetic mice receiving a Pluronic gel containing either control oligonucleotide (NT) or 2'OMe-miR-222 (AS). After 7 days, levels of mRNA encoding the targets of miR-221/222, $P27^{Kip1}$, c-Kit, and PUMA were measured using quantitative real-time PCR with HPRT1 as a loading control. Data is normalized to the ND. Data represent the mean±SEM and † indicates p<0.05 by ANOVA using Tukey's HSD.
Figure 9:
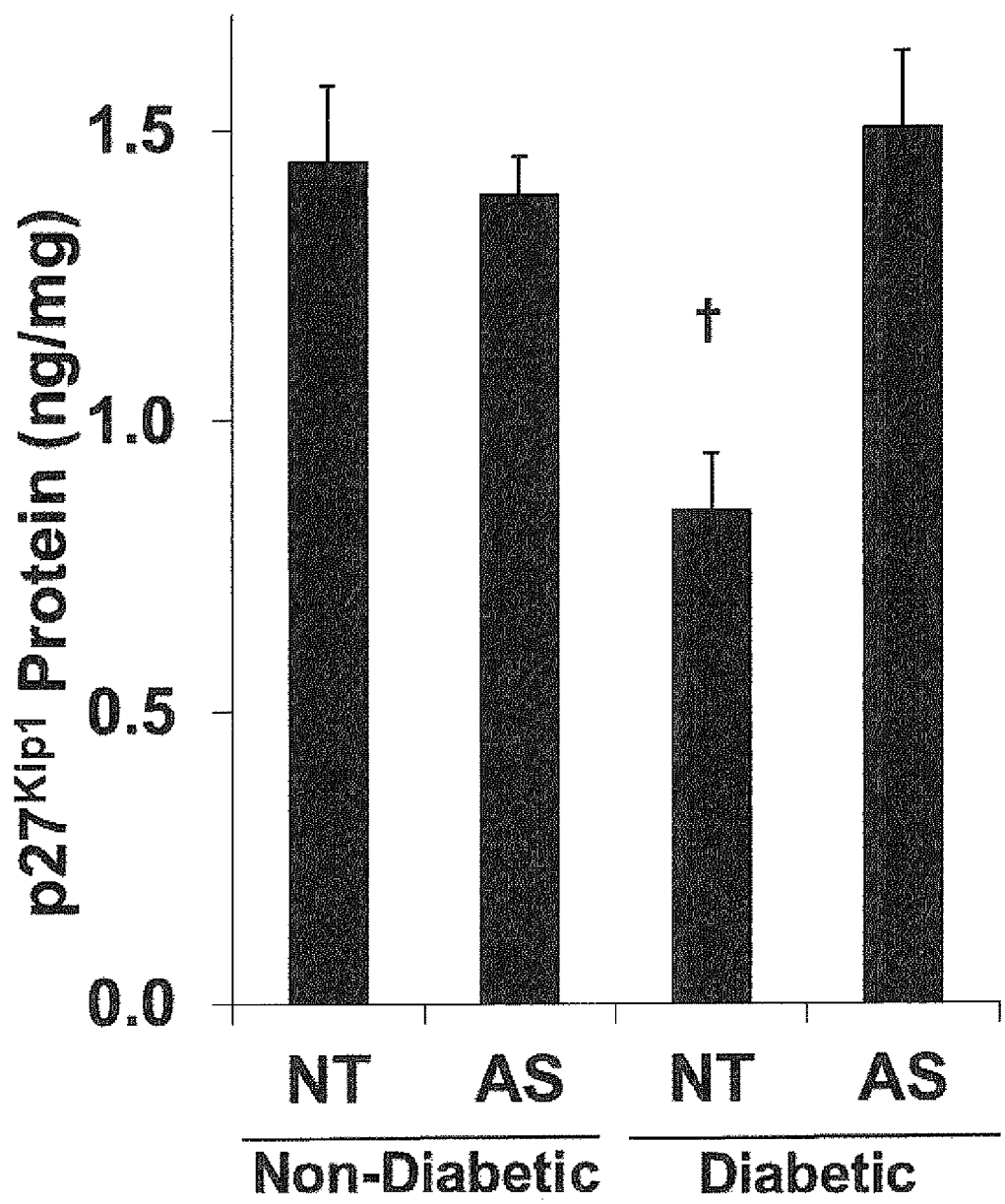
FIG. 9. Diabetes induces an increase in miR-221/222 that reduces $p27^{Kip1}$ levels in arteries Protein lysates were prepared from injured femoral arteries of diabetic and non-diabetic mice receiving a Pluronic gel containing either control oligonucleotide (NT) or 2'OMe-miR-222 (AS) after 7 days. Levels of $p27^{Kip1}$ protein levels were measured using an ELISA kit. Data is normalized to the ND. Data represent the mean±SEM and † indicates p<0.05 by ANOVA using Tukey's HSD.
Figure 10:
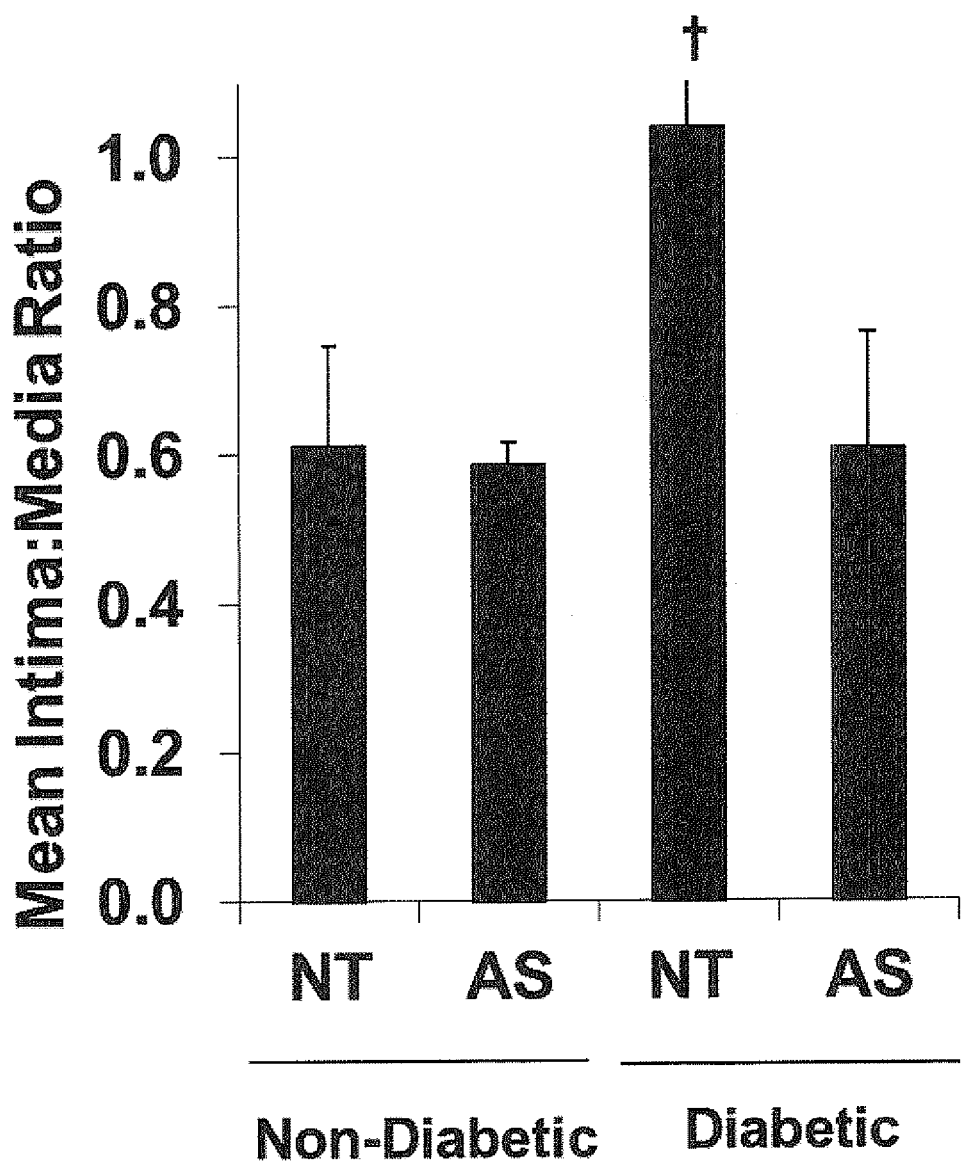
FIG. 10. Diabetes induces an increase in miR-221/222 that increases intimal thickening. Intimal thickening was measured in the wire injured femoral arteries of diabetic and non-diabetic mice receiving a Pluronic gel containing either control oligonucleotide (NT) or 2'OMe-miR-222 (AS) after 14 days. Data represent the mean±SEM and † indicates p<0.05 by ANOVA using Tukey's HSD.

FIG. 8 demonstrates that the increase in miR-221/222 diminishes its targets, $p27^{Kip1}$, c-Kit, and the p53-up-regulated modulator of apoptosis (PUMA). This in turn promotes cell proliferation and migration. FIG. 9 demonstrates that inhibition of miR-221/222 with 2'OMe-miR-222 restores levels of $p27^{Kip1}$ protein to normal levels. FIG. 10 demonstrates that reducing miR-221/222 levels to the levels seen in non-diabetic mice is effective at reducing intimal thickening in the diabetic mice to levels similar to that of normal mice.

Figure 11:
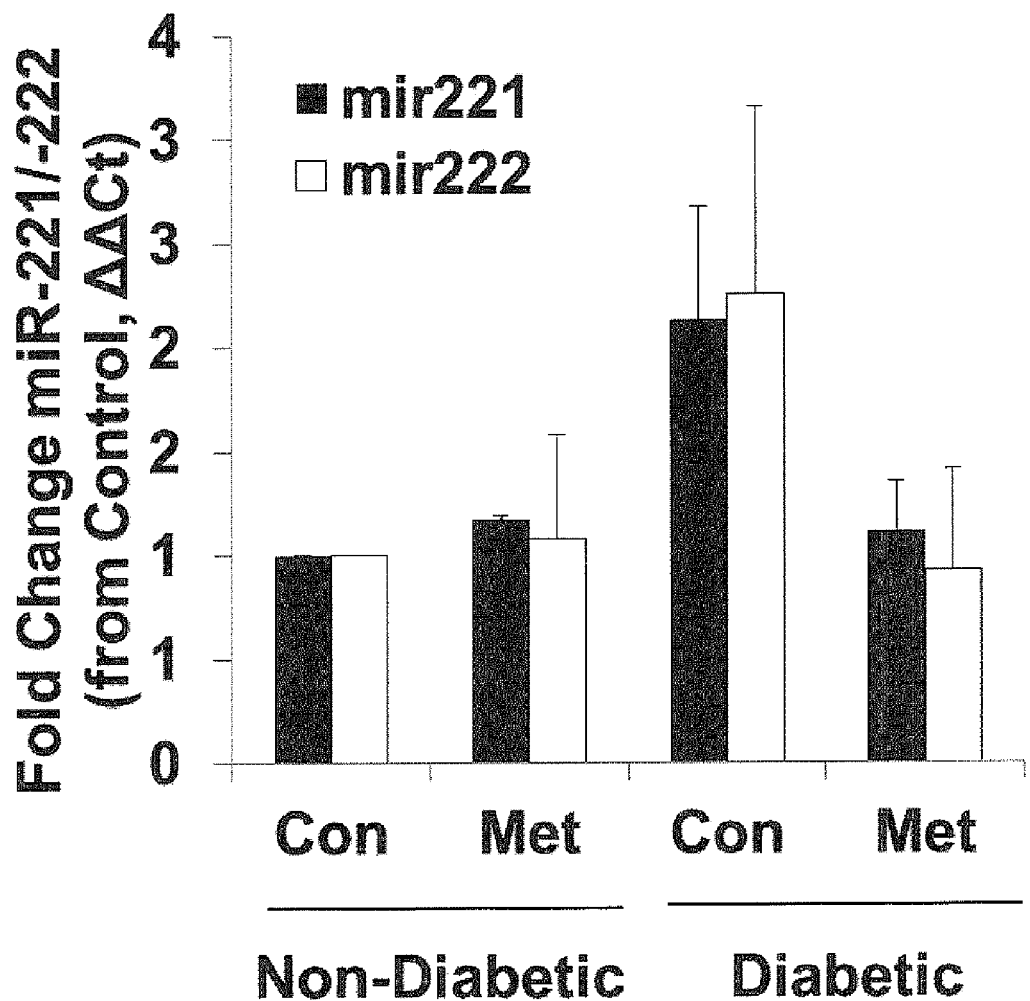
FIG. 11. The increase in miR-221/222 in VSMCs from the DM mice is reversed by AMPK activation. miR-221/222 levels were measured in VSMCs from non-diabetic and diabetic mice incubated with vehicle (Con) and the AMPK agonist, Metformin (Met) for 3 h. Data represent the mean±SEM.
Figure 12:
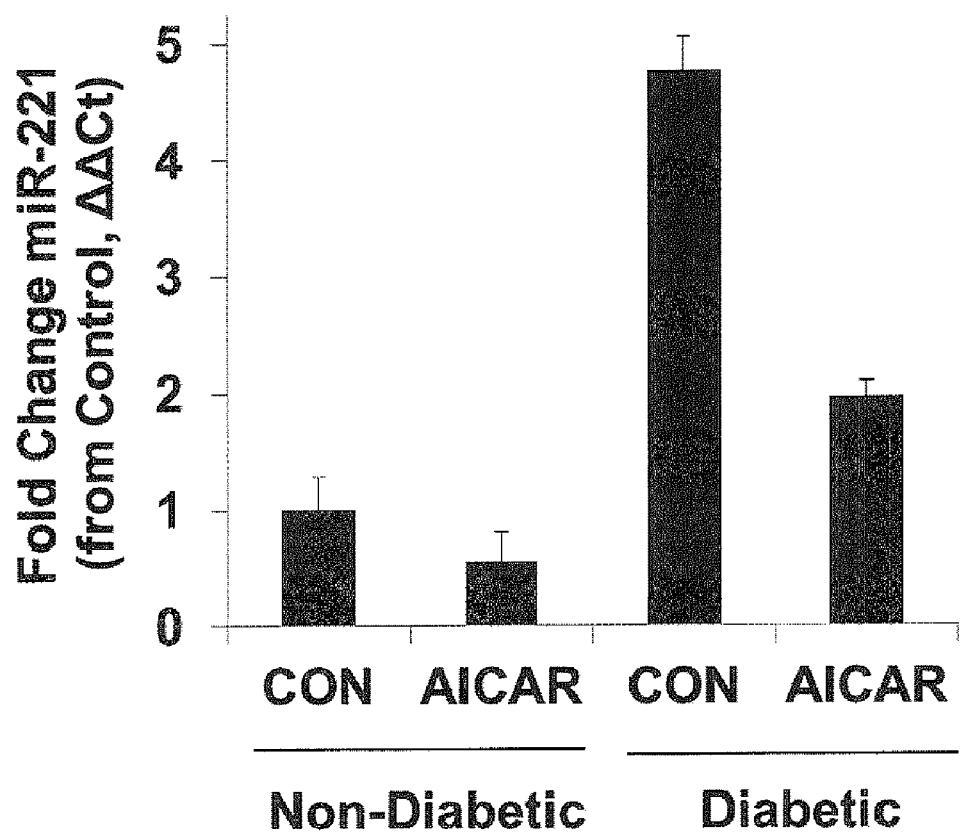
FIG. 12. The increase in miR-221/222 in VSMCs from the DM mice is reversed by AMPK activation. miR-221/222 levels were measured in VSMCs from non-diabetic and diabetic mice incubated with vehicle (Con) and the AMPK agonist, AICAR for 3 h. Data represent the mean±SEM.
Figure 13:
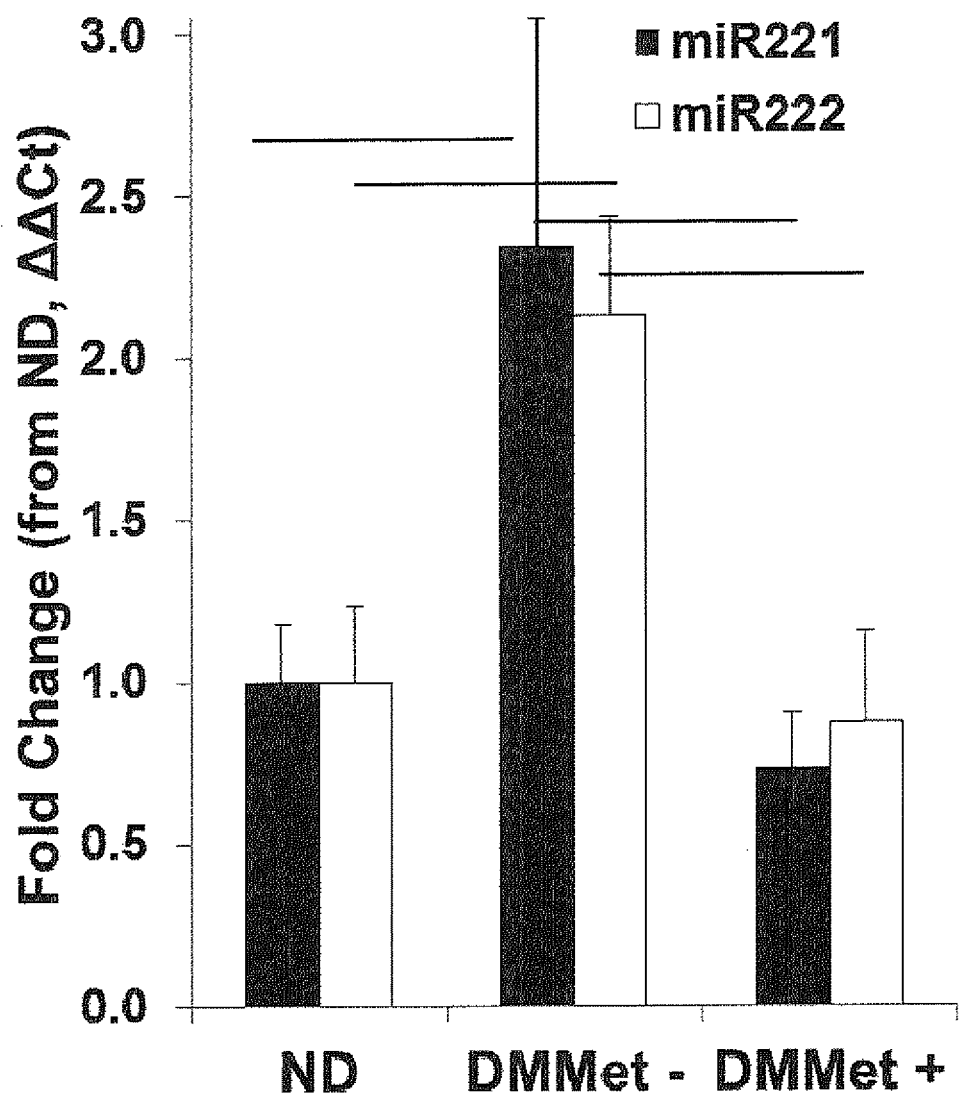
FIG. 13. miR-221/222 are reduced in the vasculature of diabetic patients taking the AMPK agonist metformin. miR-221/222 levels were measured using real-time PCR methods in the internal mammary arteries of non-diabetic (ND), diabetic subjects currently taking metformin (DMMet+), and diabetic subjects not taking metformin (DMMet−) undergoing coronary artery bypass surgery. The DMMet− group exhibited a significant increase in miR-221/222 compared to ND, while the DMMet+ group exhibited miR-221/222 levels similar to ND. Data represent the mean±SEM.

One embodiment of the invention is a method comprising agonists of 5' adenosine monophosphate-activated protein kinase (AMPK) to block the increase in ERK activity and reduce miR-221/222 expression. AMPK activation reduces ERK activation in response to IGF-1 (35). FIGS. 11 and 12 demonstrate that two AMPK agonists, metformin and AICAR (respectively), are effective in reducing miR-221/222 in the VSMCs from diabetic mice to levels similar to VSMCs from non-diabetic mice. FIG. 13 demonstrates that among patients undergoing coronary artery bypass grafting, those diabetic patients that are not currently taking metformin exhibit elevated levels of miR-221/222 in their internal mammary arteries. Furthermore, those diabetic patients currently on metformin therapy exhibited normal levels of miR-221/222 in their internal mammary arteries.

Our data show that in a mouse model of type 2 diabetes, neointimal hyperplasia following femoral wire injury is increased in manner resistant to mTOR inhibition. This resistance to mTOR inhibition is derived from the down-regulation of $p27^{Kip1}$ in an mTOR independent manner by the increased miR-221/222 levels caused by increased ERK activity. This invention describes the use of methods that inhibit activation of the ERK pathway or promote activation of the AMPK pathway to block the increase in miR-221/222, inhibit the increase in intimal thickening associated with diabetes and restoring the normal response of the vasculature to mTOR As intimal thickening is the major component of restenosis, one embodiment of this invention is the use of a miR-221/222 lowering agents in combination with an mTOR inhibitor for the prevention of restenosis in patients with diabetes. The miR-221/222 lower agent may be an ERK pathway inhibitor, an AMPK agonist, or a silencing RNA directly targeting miR-221/222. The mTOR inhibitor to be combined with the miR-221/222 lowering agent could be selected from a group consisting of BEZ235 (NVP-BEZ235), Everolimus (RAD001), Rapamycin (Sirolimus, AY-22989, WY-090217), AZD8055, Temsirolimus (CCI-779, Torisel), PI-103, KU-0063794, Deforolimus (Ridaforolimus, AP23573, MK-8669), PP242, XL765, GSK1059615, WYE-354, OSI-027, GDC-0980 (RG7422), GSK2126458, PKI-587, PF-04691502, WYE-125132, WYE-687, NVP-BGT226, WAY-600, AZD2014, INK 128, Torin1. As the standard method for administering mTOR inhibitors for the prevention of restenosis is drug eluting stents, an embodiment of this invention is an intraluminal device impregnated with and configured to release a compound that inhibits increases in miR-221 and/or miR-222 in the vasculature and an mTOR inhibitor. The addition of the miR-221/222 lowering agent restore normal regulation of intimal thickening that is sensitive to mTOR inhibition making the standard anti-restenotic therapies effective in diabetic patients.

EXAMPLES

Figure 14:
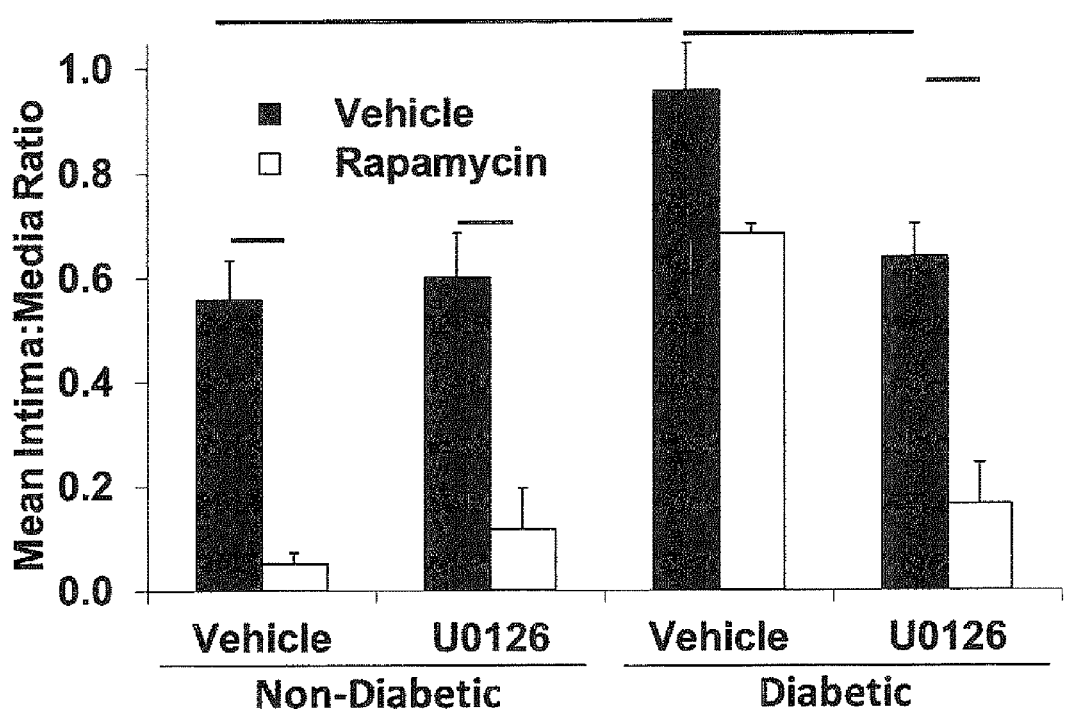
FIG. 14. Inhibition of ERK activity reduces intimal hyperplasia following wire injury and restores sensitivity to rapamycin in the DM mice. Mean intima:media ratios of ND and DM mice following femoral artery wire injury and implantation of a Pluronic-F 127 gel containing either vehicle or rapamycin (100 μg) with and without administration of the ERK pathway inhibitor, U0126 (7.5 mg/kg/d). Bars indicate p<0.05 by ANOVA.

FIG. 14 illustrates an example of the present invention. In non-diabetic mice local delivery of rapamycin is highly effective at reducing intimal thickening in response to wire injury. In diabetic mice, intimal thickening is increased and local delivery of rapamycin is no longer effective at reducing intimal thickening. Co-administration of the MEK 1/2 inhibitor, U0126, has minimal effects in the non-diabetic mice, but restores the ability of rapamycin to intimal thickening in the diabetic mice.

REFERENCES

1. Roger V L, et al. (2012) Heart disease and stroke statistics—2012 update: a report from the American Heart Association. *Circulation* 125(1):e2-e220.

2. Nakashima Y, Chen Y X, Kinukawa N, & Sueishi K (2002) Distributions of diffuse intimal thickening in human arteries: preferential expression in atherosclerosis-prone arteries from an early age. *Virchows Arch* 441(3): 279-288.
3. Nakashima Y, Fujii H, Sumiyoshi S, Wight T N, & Sueishi K (2007) Early human atherosclerosis: accumulation of lipid and proteoglycans in intimal thickenings followed by macrophage infiltration. *Arterioscler Thromb Vasc Biol* 27(5):1159-1165.
4. Nakashima Y, Wight T N, & Sueishi K (2008) Early atherosclerosis in humans: role of diffuse intimal thickening and extracellular matrix proteoglycans. *Cardiovasc Res* 79(1):14-23.
5. Schwartz S M, Galis Z S, Rosenfeld M E, & Falk E (2007) Plaque rupture in humans and mice. *Arterioscler Thromb Vasc Biol* 27(4):705-713.
6. Jackson C L, Bennett M R, Biessen E A, Johnson J L, & Krams R (2007) Assessment of unstable atherosclerosis in mice. *Arterioscler Thromb Vasc Biol* 27(4):714-720.
7. Collet C A, et al. (2011) Assessing the temporal course of neointimal hyperplasia formation after different generations of drug-eluting stents. *JACC Cardiovasc Interv* 4(10):1067-1074.
8. Kornowski R, et al. (1997) Increased restenosis in diabetes mellitus after coronary interventions is due to exaggerated intimal hyperplasia. A serial intravascular ultrasound study. *Circulation* 95(6):1366-1369.
9. Koyama H, Olson N E, Dastvan F F, & Reidy M A (1998) Cell replication in the arterial wall: activation of signaling pathway following in vivo injury. *Circ Res* 82(6):713-721.
10. Ahanchi S S, et al. (2008) Heightened efficacy of nitric oxide-based therapies in type II diabetes mellitus and metabolic syndrome. *Am J Physiol Heart Circ Physiol* 295(6):H2388-2398.
11. Lightell D J, Jr., Moss S C, & Woods T C (2011) Loss of Canonical Insulin Signaling Accelerates Vascular Smooth Muscle Cell Proliferation and Migration Through Changes in p27Kip1 Regulation. *Endocrinology* 152:651-658.
12. Lightell D J, Jr. & Woods T C (2013) Relative Resistance to mTOR Inhibition in Vascular Smooth Muscle Cells of Diabetic Donors. *Ochsner J* 13(1):56-60.
13. Wang C C, Gurevich I, & Draznin B (2003) Insulin affects vascular smooth muscle cell phenotype and migration via distinct signaling pathways. *Diabetes* 52(10): 2562-2569.
14. Nilsson-Berglund L M, et al. (Nuclear factor of activated T cells regulates osteopontin expression in arterial smooth muscle in response to diabetes-induced hyperglycemia. *Arterioscler Thromb Vasc Biol* 30(2):218-224.
15. Wendt T, et al. (2002) Receptor for advanced glycation endproducts (RAGE) and vascular inflammation: insights into the pathogenesis of macrovascular complications in diabetes. *Curr Atheroscler Rep* 4(3):228-237.
16. Jones J I, Prevette T, Gockerman A, & Clemmons D R (1996) Ligand occupancy of the alpha-V-beta3 integrin is necessary for smooth muscle cells to migrate in response to insulin-like growth factor. *Proc Natl Acad Sci USA* 93(6):2482-2487.
17. Maile L A, Capps B E, Ling Y, Xi G, & Clemmons D R (2007) Hyperglycemia alters the responsiveness of smooth muscle cells to insulin-like growth factor-I. *Endocrinology* 148(5):2435-2443.
18. Folli F, Kahn C R, Hansen H, Bouchie J L, & Feener E P (1997) Angiotensin II inhibits insulin signaling in aortic smooth muscle cells at multiple levels. A potential role for serine phosphorylation in insulin/angiotensin II crosstalk. *J Clin Invest* 100(9):2158-2169.
19. Inoguchi T, et al. (2000) High glucose level and free fatty acid stimulate reactive oxygen species production through protein kinase C-dependent activation of NAD(P)H oxidase in cultured vascular cells. *Diabetes* 49(11):1939-1945.
20. Nakanishi H, Brewer K A, & Exton J H (1993) Activation of the zeta isozyme of protein kinase C by phosphatidylinositol 3,4,5-trisphosphate. *J Biol Chem* 268(1):13-16.
21. Taniyama Y, Hitomi H, Shah A, Alexander R W, & Griendling K K (2005) Mechanisms of reactive oxygen species-dependent downregulation of insulin receptor substrate-1 by angiotensin II. *Arterioscler Thromb Vasc Biol* 25(6):1142-1147.
22. Preis S R, et al. (2009) Trends in all-cause and cardiovascular disease mortality among women and men with and without diabetes mellitus in the Framingham Heart Study, 1950 to 2005. *Circulation* 119(13):1728-1735.
23. Kim T N, et al. (2010) Vascular inflammation in patients with impaired glucose tolerance and type 2 diabetes: analysis with 18F-fluorodeoxyglucose positron emission tomography. *Circ Cardiovasc Imaging* 3(2):142-148.
24. Chen D, et al. (1997) Downregulation of cyclin-dependent kinase 2 activity and cyclin A promoter activity in vascular smooth muscle cells by p27(KIP1), an inhibitor of neointima formation in the rat carotid artery. *J Clin Invest* 99(10):2334-2341.
25. Gallo R, et al. (1999) Inhibition of intimal thickening after balloon angioplasty in porcine coronary arteries by targeting regulators of the cell cycle. *Circulation* 99(16): 2164-2170.
26. Luo Y, et al. (1996) Rapamycin resistance tied to defective regulation of p27Kip1. *Mol Cell Biol* 16(12): 6744-6751.
27. Marx S O, Jayaraman T, Go L O, & Marks A R (1995) Rapamycin-FKBP inhibits cell cycle regulators of proliferation in vascular smooth muscle cells. *Circ Res* 76(3): 412-417.
28. Sun J, et al. (2001) Role for p27(Kip1) in Vascular Smooth Muscle Cell Migration. *Circulation* 103(24): 2967-2972.
29. Tanner F C, et al. (1998) Expression of cyclin-dependent kinase inhibitors in vascular disease. *Circ Res* 82(3):396-403.
30. Moses J W, et al. (2003) Sirolimus-eluting stents versus standard stents in patients with stenosis in a native coronary artery. *N Engl J Med* 349(14):1315-1323,
31. Poon M, et al. (1996) Rapamycin inhibits vascular smooth muscle cell migration. *J Clin Invest* 98(10):2277-2283.
32. Weisz G., et al. (2006) Two-year outcomes after sirolimus-eluting stent implantation: results from the Sirolimus-Eluting Stent in de Novo Native Coronary Lesions (SIRIUS) trial. *J Am Coll Cardiol* 47(7):1350-1355.
33. Jonas M, et al. (2005) Vascular neointimal formation and signaling pathway activation in response to stent injury in insulin-resistant and diabetic animals. *Circ Res* 97(7): 725-733.
34. Krutzfeldt J, et al. (2005) Silencing of microRNAs in vivo with 'antagomirs'. *Nature* 438(7068):685-689.
35. Motobayashi Y, et al. (2009) Adiponectin inhibits insulin-like growth factor-1-induced cell migration by the suppression of extracellular signal-regulated kinase 1/2 activation, but not Akt in vascular smooth muscle cells. *Hypertens Res* 32(3):188-193.

The invention claimed is:

1. A method for improving the efficacy of mammalian Target of Rapamycin inhibitors to prevent increased intimal thickening through the inhibition of vascular smooth muscle cell proliferation and migration in subjects with diabetes mellitus comprising administering a therapeutically effective amount of a composition that reduces miR-221 and/or miR-222 levels in the vasculature.

2. The method according to claim 1, wherein the composition reduces miR-221 and/or miR-222 levels by silencing RNA molecule targeting miR-221 or miR-222, and the composition is 2'OMe-miR-222.

3. The method according to claim 1, wherein the composition reduces miR-221 and/or miR-222 levels by silencing RNA molecule targeting miR-221 or miR-222 wherein the composition is of the ribonucleic acid sequence: SEQ ID NO: 1 5'-ACCCAGUAGCCAGAUGUAGCU-3'.

4. The method according to claim 3, wherein the ribonucleic acid has a phosphorothioate backbone according to SEQ ID NO: 2.

5. The method according to claim 3, wherein the ribonucleic acid has a locked nucleic acid backbone according to SEQ ID NO: 3.

6. The method according to claim 3, wherein the ribonucleic acid includes a 2'methylated backbone according to SEQ ID NO: 4.

* * * * *